(12) United States Patent
Jung et al.

(10) Patent No.: US 7,678,579 B2
(45) Date of Patent: Mar. 16, 2010

(54) METHOD FOR ANALYSIS METABOLITE DIFFERENCE BETWEEN BIOLOGICAL SAMPLES

(75) Inventors: Byung Hwa Jung, Seoul (KR); Bong Chul Chung, Namyangju-si (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 11/784,292

(22) Filed: Apr. 5, 2007

(65) Prior Publication Data

US 2008/0076181 A1 Mar. 27, 2008

(30) Foreign Application Priority Data

Sep. 27, 2006 (KR) .................... 10-2006-0094002

(51) Int. Cl.
*G01N 30/02* (2006.01)

(52) U.S. Cl. .................... 436/161; 436/2; 436/178

(58) Field of Classification Search ............ 422/70, 422/59, 89; 73/19.02, 23.22, 23.35, 23.37, 73/61.52; 210/634, 635, 645, 656, 198.2; 436/2, 161, 178
See application file for complete search history.

(56) References Cited

U.S. PATENT DOCUMENTS

| 7,072,773 B2 * | 7/2006 | Plumb et al. .................. 702/32 |
| 2006/0292572 A1 * | 12/2006 | Stuart et al. ..................... 435/6 |
| 2007/0031517 A1 * | 2/2007 | Matar et al. ................. 424/733 |

FOREIGN PATENT DOCUMENTS

WO WO 02/057989 A2 7/2002

OTHER PUBLICATIONS

Determination of Alachlor and Two Metabolites in Ground Water Using Solid Phase and a new Micro-Liquid-Liquid Extraction Method. Regine Heyer, Andreas Zapf, H.J. Stan Fresenius J Anal Chem. (1995) 351:752-757.*

(Continued)

*Primary Examiner*—Robert J Hill, Jr.
*Assistant Examiner*—Dwan A Gerido
(74) *Attorney, Agent, or Firm*—Fenwick & West LLP

(57) ABSTRACT

Disclosed is a method of extracting all metabolites existing in a biological sample to detect a comprehensive difference between metabolites of a control group and a test group, thereby verifying significance thereof. More particularly, the invention comprises a first step of analyzing a fraction extracted with a solid phase extraction method, a fraction obtained by extracting the remnant fraction with a liquid-liquid extraction method and fractions extracted with the liquid-liquid extraction method at two pH different from each other after the hydrolysis, with a gas chromatography-mass spectrometry; a second step of converting the chromatogram result into numerical values capable of being statistically processed; and a third step of analyzing the numerical values with a principal component analysis (PCA) and a discriminant analysis (DA) to detect a difference between the control group and the test group. According to the invention, the difference between the two groups can be comprehensively detected with the areas of the peaks on the chromatogram, without a standard material or verified quantitative method. Therefore, it is possible to detect the metabolic change in the organism due to the disease or gene mutation, without an accurate quantitative analysis of the metabolites.

4 Claims, 5 Drawing Sheets

OTHER PUBLICATIONS

On the Metabolism of the Amphetamine-Derived Antispasmodic Drug Mebeverine: Gas Chromatography-Mass Spectrometry Studies on Rat Liver Microsomes and on Human Urine Thomas Kraemer, Joerg Bickeboeller-Friedrich, Hans Maurer Drug Metabolism and Disposition vol. 28, No. 3, 339-347.*

Castrillo, J., et al., "An Optimized Protocol for Metabolome Analysis in Yeast Using Direct Infusion Electrospray Mass Spectrometry," Phytochemistry 62, pp. 929-937 (2003).

Sumner, L., et al., "Plant Metabolomics: Large-Scale Phytochemistry in the Functional Gemonics Era," Phytochemistry 62, pp. 817-836 (2003).

Yamazaki, M., et al., "Metabolomics and Differential Gene Expression in Anthocyanin Chemo-Varietal Forms of Perilla frutescens," Phytochemistry 62, pp. 987-995 (2003).

Abstract of Aharoni, A. et al., "Nontargeted Metabolome Analysis by Use of Fourier Transform Ion Cyclotron Mass Spectrometry," Journal of Integrative Biology, vol. 6, No. 3, pp. 217-234 (2002).

Baggett, B., et al., "Profiling Isoflavonoids Found in Legume Root Extracts Using Capillary Electrophoresis," Electrophoresis, vol. 23, pp. 1642-1651 (2002).

Fiehn, O., et al., "Metabolite Profiling for Plant Functional Genomics," Nature Biotechnology, vol. 18, pp. 1157-1161 (Nov. 2000).

Soo, E., et al., "Selective Detection and Identification of Sugar Necleotides by CE—Electrospray-MS and Its Application to Bacterial Metabolomics," Analytical Chemistry, vol. 76, No. 3, pp. 619-626 (Feb. 1, 2004).

"Meeting Report—Plant Metabolomics: The Missing Link in Functional Genomics Strategies," The Plant Cell, vol. 14, pp. 1437-1440 (Jul. 2002).

Griffiths, J., et al., "Opportunities for Studying Cancer by Metabolomics: Preliminary Observations on Tumors Deficient in Hypoxia-Inducible Factor 1," Advances in Enzyme Regulation, vol. 43, pp. 67-76(2003).

Verhoeckx, K., et al., "Characterization of Anti-Inflammatory Compounds Using Transcriptomics, Proteomics, and Metabolomics in Combination with Multivariate Data Analysis," International Immunopharmacology, vol. 4, pp. 1499-1514 (2004).

Aharoni, A., et al., "Nontargeted Metabolome Analysis by Use of Fourier Transform Ion Cyclotron Mass Spectrometry," OMICS, A Journal of Integrative Biology, 2002, pp. 217-234, vol. 6, No. 3 (Full Text).

Kanani, H. H., et al., "Data Correction Strategy for Metabolomics Analysis Using Gas Chromatography-Mass Spectrometry," Metabolic Engineering, 2007 (available online on Aug. 18, 2006), pp. 39-51, vol. 9.

Jonsson, P., et al., "A Strategy for Identifying Differences in Large Series of Metabolomic Samples Analyzed by GC/MS," Analytical Chemistry, Mar. 15, 2004, pp. 1738-1745, vol. 76, No. 6.

Jonsson, P., et al., "High-Throughput Data Analysis for Detecting and Identifying Differences Between Samples in GC/MS-Based Metabolomic Analyses," Analytical Chemistry, Sep. 1, 2005, pp. 5635-5642, vol. 77, No. 17.

Kim, Jin Young, et al., "Simultaneous determination of carisoprodol and meprobamate in human hair using solid-phase extraction and gas chromatography/mass spectrometry of the trimethylsilyl derivatives," Rapid Communications in Mass Spectrometry, Nov. 15, 2005, pp. 3056-3062, vol. 19, No. 21, John Wiley & Sons, Ltd., New York, NY, USA.

Cone, E. J., et al., "Assay for codeine, morphine and ten potential urinary metabolites by gas chromatography-mass fragmentography," Journal of Chromatography, Jul. 8, 1983, pp. 307-318, vol. 275, No. 2, Elsevier Science Publishers B.V., Amsterdam, The Netherlands.

* cited by examiner

• NORMAL ■ PATIENT

• NORMAL    ■ PATIENT

• NORMAL   ■ PATIENT

• NORMAL   ■ PATIENT

METHOD FOR ANALYSIS METABOLITE DIFFERENCE BETWEEN BIOLOGICAL SAMPLES

CROSS-REFERENCE TO RELATED APPLICATION

This application claims all benefits of Korean Patent Application No. 10-2006-0094002 filed on Sep. 27, 2006 in the Korean Intellectual Property Office, the disclosures of which are incorporated herein by reference.

BACKGROUND OF THE INVENTION

1. Field of the Invention

The invention relates to a method of extracting all metabolites existing in a biological sample to detect a comprehensive difference between metabolites of a control group and a test group, thereby verifying significance thereof. The biological sample being analyzed by the invention includes all materials existing in an organism, such as blood, blood plasma, serum, urine, feces, cerebrospinal fluid, tissue, hair, serous fluid, gastric juice and the like.

2. Description of the Related Art

Until now, a research using metabolite is mainly concentrated on a targeted metabolomics research of quantitatively analyzing a reference standard of a specific metabolome in a cell under disease state or gene mutated state and then comparing changes in an amount or concentration of metabolites of a test group and a control group or a ratio of amounts or concentrations of metabolites related to a metabolic pathway, so as to clarify a defect occurring in the metabolic pathway when a disease or gene mutation occurs and to induce a disease diagnosis biomarker using it.

However, there are various metabolites in the organism and it is very difficult in a test to acquire a reference standard of all the metabolites and to conduct a quantitative analysis of it. Accordingly, it has appeared a global metabolomics research as a non-targeted metabolomics, which is capable of verifying a change of the metabolites in the organism on the whole without the complicated analysis steps.

Actually, such research has been much conducted for a bacteria or plant in which the number of the metabolites existing in the organism is relatively small [Phytochemistry, 62, 929-937 (2003); Phytochemistry, 62, 817-836 (2003); Phytochemistry, 62, 987-995 (2003); Journal of Integrative Biology, 6, 217-234 (2002); Electrophoresis, 23, 1642-1651 (2002); Nature Biotechnology, 18, 1157-1161 (2000); Anal. Chem., 76, 619-626 (2004); Plant Cell, 14, 1437-1440 (2002); Advan. Enzyme Regul. 43, 67-76 (2003); International Immunopharmacology, 4, 1499-1514 (2004)]. However, regarding all the animal samples including human, an extract method and an analysis are complicated, there are differences between the individual organisms and an analysis method which is an indicator does not exist, so that the above research has not been almost applied.

Therefore, it is seriously needed to standardize a method of extracting a biological sample and to develop a method of connecting a device analysis and statistics enabling a metabolite profiling of a test group and a control group, which is obtained by a device analysis chromatogram, to be statistically analyzed.

SUMMARY OF THE INVENTION

In order to solve the above problem, an object of the invention is to provide a method for defining and using a standard extraction method so as to extract all metabolites from a biological sample as much as possible, obtaining a chromatogram with a chromatography analysis device, digitizing the chromatogram so that it can be statistically processed, and detecting a significant difference between a control group and a test group with a principle component analysis (PCA) and a discriminant analysis (DA).

In order to achieve the above object, there is provided a method for detecting a difference between two biological sample groups, the method comprising extracting a metabolite from a biological sample by applying sequentially (i) a solid phase extraction method, (ii) a liquid-liquid extraction method in a weak acid, (iii) a liquid-liquid extraction method in a weak acid after hydrolysis and (iv) a liquid-liquid extraction method in a base.

According to the invention, the method for detecting additionally comprises analyzing the extracted metabolite with a chromatography analysis device; converting the chromatography analysis result into numerical values capable of being statistically processed; and statistically verifying a difference between the two biological sample groups with the converted numerical values.

According to the invention, the weak acid of the (ii) and (iii) may mean pH 5~5.5 and the base of the (iv) may mean pH 13~13.5.

According to the invention, the chromatography analysis device may have a mass spectrometry mounted to a gas chromatography.

According to the invention, $\beta$-glucuronidase and arylsulfatase may be used in the hydrolysis of the (iii).

According to the invention, for converting, a total analysis time may be divided by a unit time interval and the highest value of areas or heights of chromatogram peaks exhibited during the unit time period may be determined as a representative value during the unit time period.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Figure 1:
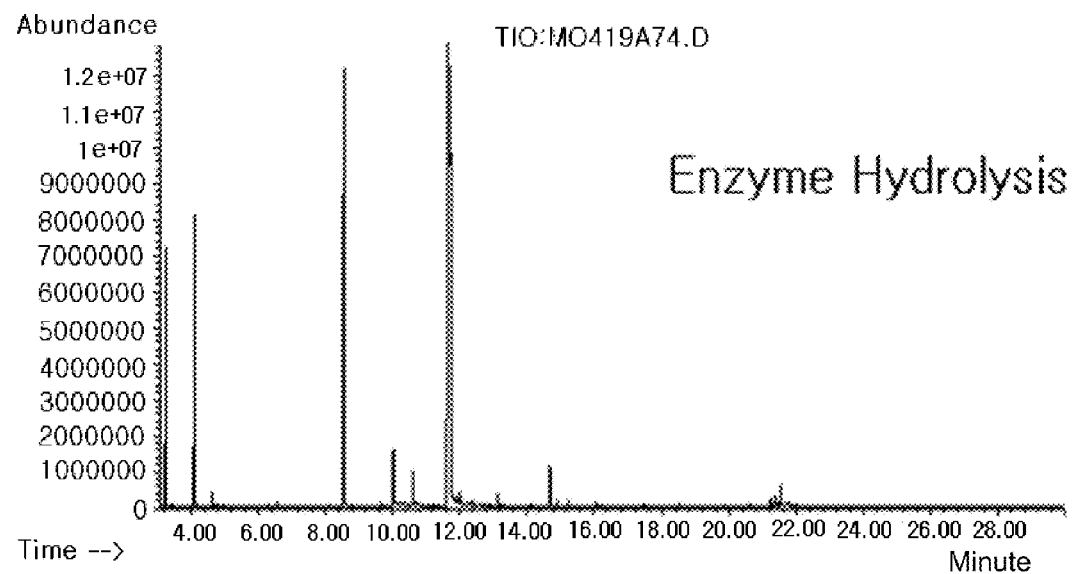
FIG. 1 is a view comparing chromatogram results so as to compare the effects of an acid hydrolysis and an enzyme hydrolysis in a step of obtaining a fraction 3.
Figure 1:
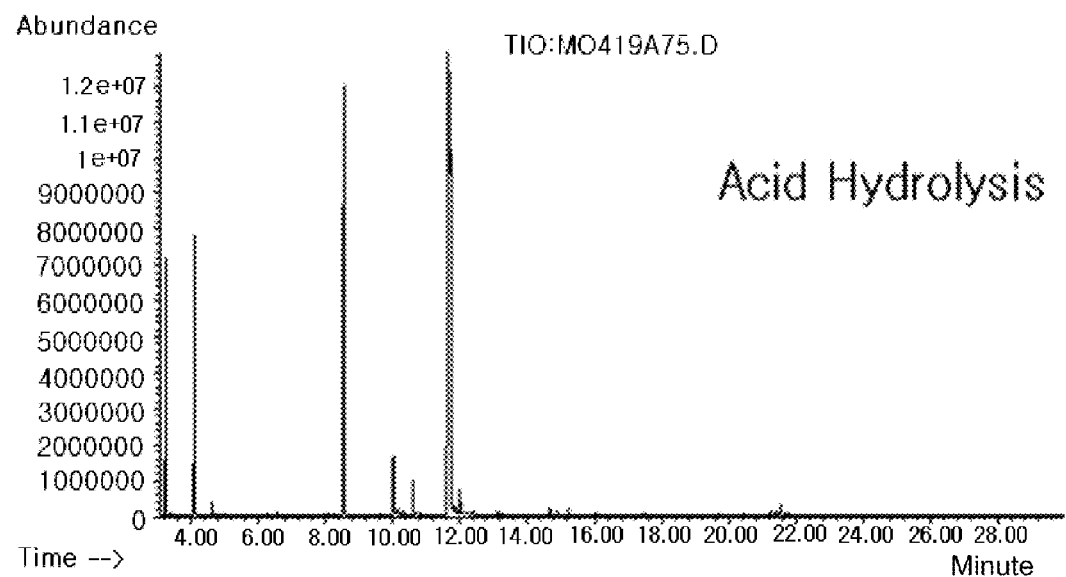

Hereinafter, a preferred embodiment of the present invention will be described with reference to the accompanying drawings.

First, a standard extraction method of a sample according to the invention is as follows. A biological sample is extracted with a solid phase extraction method (fraction 1), the remaining solution is again extracted with a liquid-liquid extraction method (fraction 2), a remaining water layer is added with enzyme to hydrolyze the conjugate existing in the biological sample and then the resulting solution is extracted with a liquid-liquid extraction method under weak acid condition (fraction 3) and it is extracted with a liquid-liquid extraction method under base condition (fraction 4).

The extracted fractions 1 to 4 are evaporated and dried to make derivatives thereof which are then analyzed with a gas chromatography-mass spectrometry. The resulting values are analyzed with a principle component analysis (PCA) and a discriminant analysis (DA), thereby verifying a difference between a control group and a test group.

The principle component analysis is a statistical technique for finding out a new principle component, which is expressed with a linear connection of variables, for the purpose of the summing-up of the materials and an easy interpretation. In other words, it is an analysis method capable of providing a means for an analysis in future. The discriminant analysis is a statistical technique of using several variable materials obtained for two or more groups to deduce a linear connection of variables exhibiting characteristics of each group, analyzing whether there is a characteristic difference, which is statistically significant, between the respective groups, using the linear connection, and expecting what group a specific observation value belongs to.

Hereinafter, the invention will be more specifically described with reference to following embodiments. However, it should be noted that they are provided to illustrate the invention, not to limit it.

Embodiment 1

Extracting a Metabolite from a Biological Sample with a Standard Extraction Method and Analyzing it with a Chromatography Analysis Device 1.1 Obtaining the Fraction 1

Strata X® (Phenomenex, Torrance, Canada; styrene-divinyl benzene polymer having a surface specially treated for keeping an analysis material from being discharged from a cartridge using a π-π interaction) cartridge was mounted to a solid phase extraction vacuum manifold, which was added with methanol 1 ml to activate it and then washed with water 1 ml, thereby carrying out a pre-treatment. Urine 1 ml, which was obtained from 10 prostatic hypertrophy patients (average age: 60±5 years) and 10 normal males (average age: 58±7 years) whose age is matched with that of the patients, was loaded to the cartridge, water 1 ml was again added to wash it and then methanol 4 ml was made to flow, thereby discharging an analysis-object material. Among them, only 0.3 ml was taken and evaporated and dried with a vacuum rotary evaporator and the remnant thereof was added with a derivatizing reagent 50 μl having mixed MSTFA (N-Methyl-N-(trimethylsilyl) trifluoroacetamide), $NH_4I$ (ammonium iodide) and dithiolerythritol in a ratio of 100:4:5 (v/v), which was then subject to a reaction at 60° C. for 15 minutes for the purpose of derivatization.

1-2. Obtaining the Fraction 2

The effluent remaining in the above 1-1 was evaporated and dried with the vacuum rotary evaporator and the remnant thereof was added with an acetic acid buffer solution (pH 5.2) 1 ml and then diethylether 5 ml, which was then shaken for 5 minutes, thereby carrying out a liquid-liquid extraction method. The extracted diethylether layer was centrifugally separated at 2500 rpm for 5 minutes, which was then again evaporated and dried with the vacuum rotary evaporator. Then, the remnant thereof was added with a derivatizing reagent 50 μl having mixed MSTFA (N-Methyl-N-(trimethylsilyl) trifluoroacetamide), $NH_4I$ (ammonium iodide) and dithiolerythritol in a ratio of 100:4:5 (v/v), which was then subject to a reaction at 60° C. for 15 minutes for the purpose of derivatization.

1-3. Obtaining the Fraction 3

In order to hydrolyze the glucuronide conjugate and sulfate conjugate, which exist in the largest amount in biological samples, thereby obtaining a conjugate form of metabolites in a free form, the water layer, which remained after separating the diethylether in the above 1-2, was added with β-glucuronidase/arylsulfatase (Helix pomatia, Roche, Mannheim, Germany) 100 μl, which was then hydrolyzed at 55° C. for 3 hours.

After the hydrolysis, the solution was added with diethylether 5 ml and then shaken for 5 minutes, thereby conducting the liquid-liquid extraction method again. The extracted diethylether layer was centrifugally separated at 2500 rpm for 5 minutes, which solution was evaporated and dried with the vacuum rotary evaporator. Then, the remnant thereof was added with a derivatizing reagent 50 μl having mixed MSTFA (N-Methyl-N-(trimethylsilyl) trifluoroacetamide), $NH_4I$ (ammonium iodide) and dithiolerythritol in a ratio of 100:4:5 (v/v), which was then subject to a reaction at 60° C. for 15 minutes for the purpose of derivatization.

There are acid hydrolysis and enzyme hydrolysis as a method for obtaining the conjugate form of metabolite, which exists in the urine sample, in a free form. A test was conducted to confirm which method was effective. For the enzyme hydrolysis, the method described in the above 1-3 was used. For the acid hydrolysis, the water layer, which remained after obtaining the fraction 2 in the above 1-2, was added with 0.1N hydrochloric acid 1 ml, which was then subject to the hydrolysis at 80° C. for 1 hour. Then, after cooled to room temperature, pH thereof was adjusted to be 5.2 with 0.1N NaOH. According to a chromatogram result of the two fractions, approximately same chromatogram tendencies were exhibited as shown in FIG. 1. However, since the very small amount of metabolites is apt to be degenerated under acid condition, the enzyme hydrolysis was used finally.

1-4. Obtaining the Fraction 4

$K_2CO_3$ 100 mg was again added to the remaining water layer to make an alkaline condition of pH 13, which was then added with diethylether 5 ml and shaken for 5 minutes, thereby conducting the liquid-liquid extraction method. The extracted diethylether layer was centrifugally separated at 2500 rpm for 5 minutes, which solution was evaporated and dried with the vacuum rotary evaporator. Then, the remnant thereof was added with a derivatizing reagent 50 μl having mixed MSTFA (N-Methyl-N-(trimethylsilyl) trifluoroacetamide), $NH_4I$ (ammonium iodide) and dithiolerythritol in a ratio of 100:4:5 (v/v), which was then subject to a reaction at 60° C. for 15 minutes for the purpose of derivatization.

1.5 Analyzing the Obtained Fractions with a Chromatography Analysis Device

In order to analyze the metabolites, it was used a 6890 Plus gas chromatograph (Agilent Co., Tokyo, Japan) having a 5973 mass spectrometry (Agilent Co.) mounted thereto and a ultra 1 column (Agilent Co.) having a length of 17 m and an inner diameter of 0.2 mm and comprising a film having a thickness of 0.33 μm and coated in the column. In the analysis, an oven temperature condition of the gas chromatograph was as follows: the initial temperature was adjusted to be 100° C. and the temperature was increased to 300° C. at a rate of 10° C. per minute. Helium was used as an analyzer carrier gas and a flow rate thereof was 1 ml/minute. An introducing part of the analyzer was 250° C., a temperature of the detector was 280° C. and a split ratio was 10:1 when introducing the sample. All the samples were analyzed in a scan mode in the mass spectrometry.

Embodiment 2

Converting the Analysis Result of the Chromatography into Numerical Values which can be Statistically Processed The areas or heights of the peaks occurring in the chromatograms of the respective fractions represent the concentration or the quantity of the metabolites in the sample. Since the peaks are not always generated as a predetermined number at a fixed time, they cannot be applied to the statistical process in which the number of variables should be constant.

In order to solve the problem, the total analysis time of 30 minutes were divided at an interval of 1 minute so that the time interval was same, and one of the peaks, which occurred for 1 minute, having the largest area was determined as a representative value, thereby conducting a statistical process.

Embodiment 3

Statistically Verifying a Difference Between Two Biological Samples Using the Converted Numerical Values As the statistical process method for the global metabolomics, the principal component analysis and the discriminant analysis were used. A leave-one out method (when the number of samples is assumed to be 100, a control group is made for the 99 samples and it is determined whether the remaining one sample belongs to a normal group or a disease group) was adopted for the discriminant analysis. It was measured an accuracy in discriminating the unknown sample as a normal person or a prostatic hypertrophy patients with the results obtained from the discriminant analysis.

Figure 2:
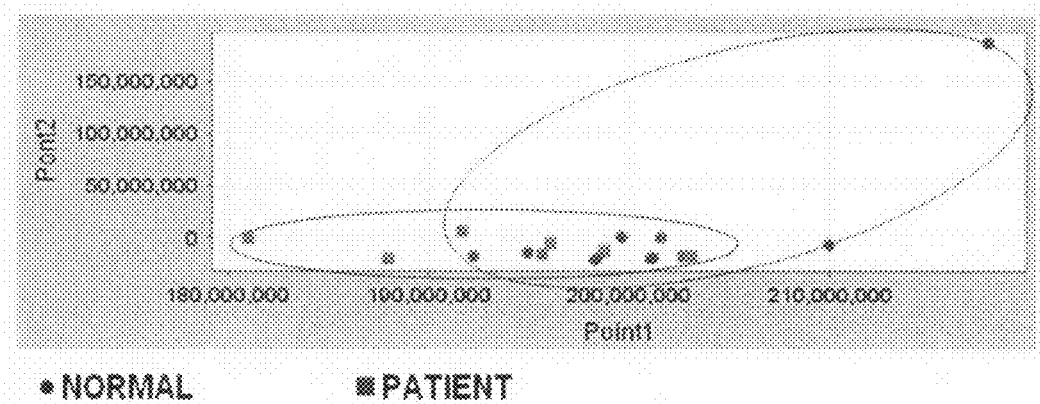
FIG. 2 shows results of a principal component analysis and a discriminant analysis, which are obtained by analyzing a fraction (fraction 1) acquired after extracting a urine sample with a solid phase extraction method.
Figure 2:
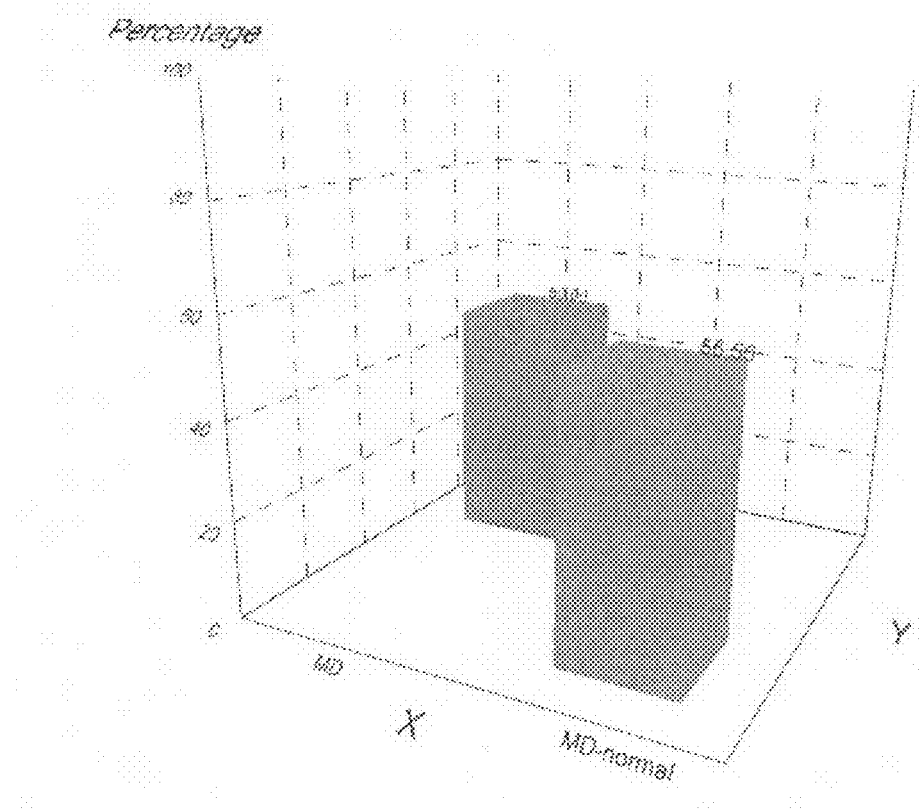
Figure 3:
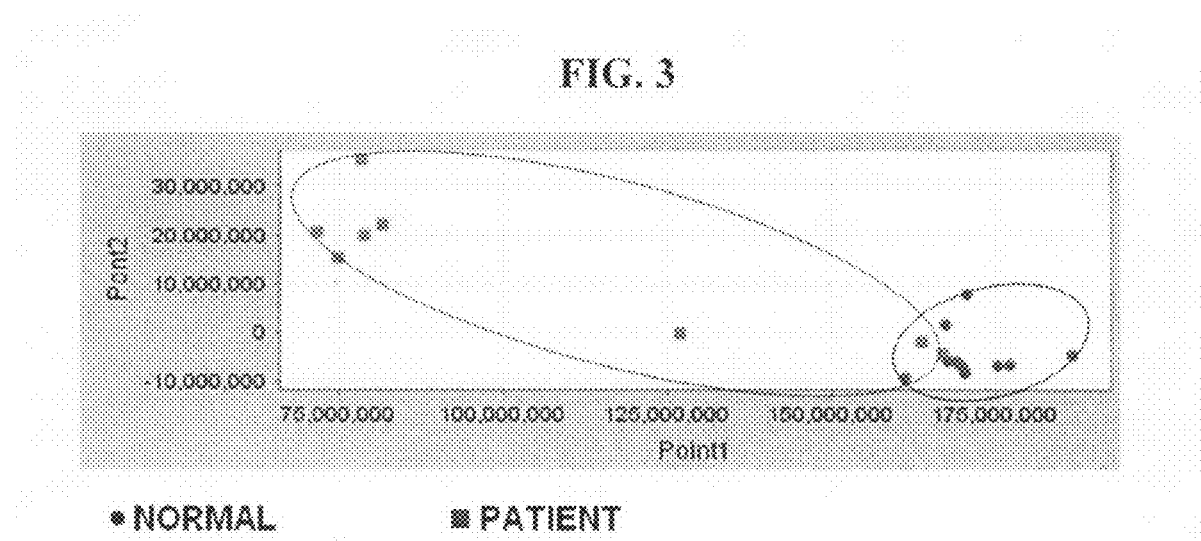
FIG. 3 shows results of a principal component analysis and a discriminant analysis, which are obtained by analyzing a fraction (fraction 2) acquired with a liquid-liquid extraction method at pH 5.2 after extracting a urine sample with a solid phase extraction method.
Figure 3:
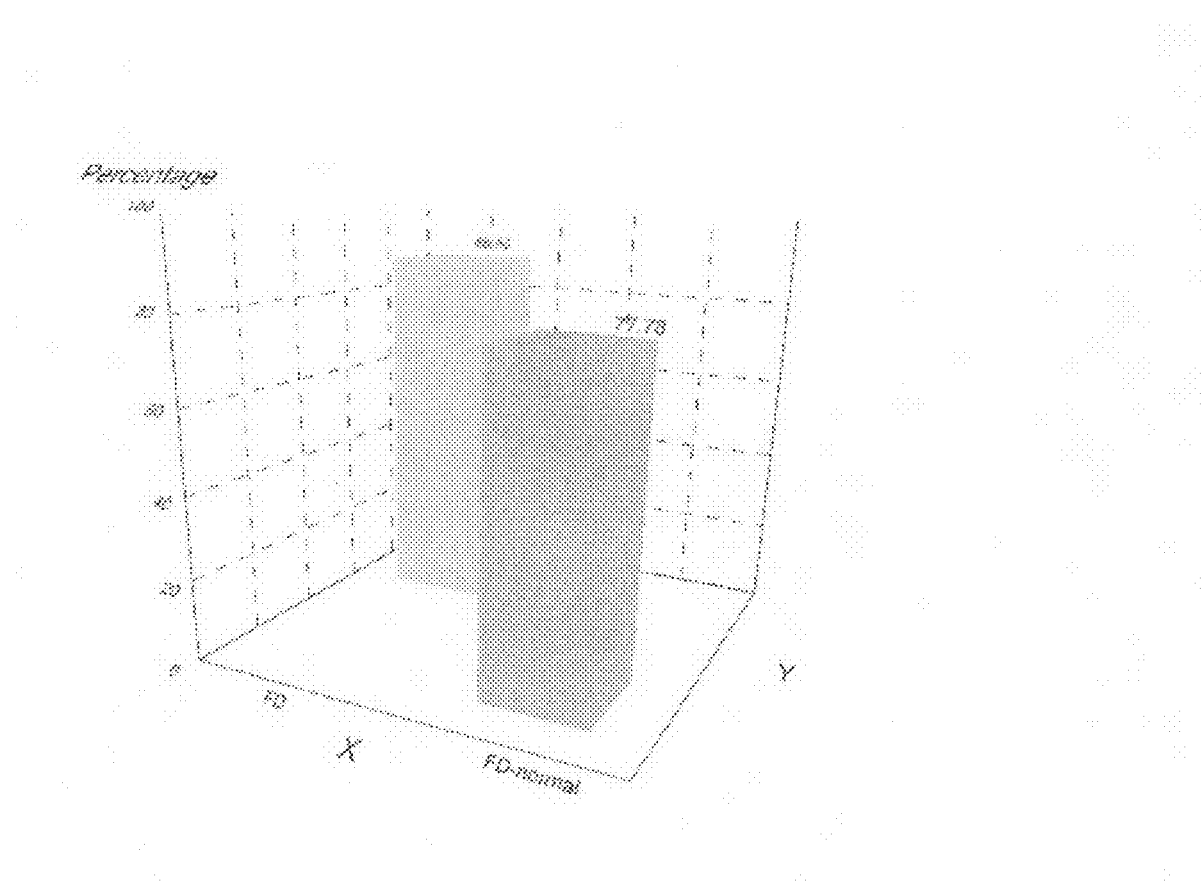
Figure 4:
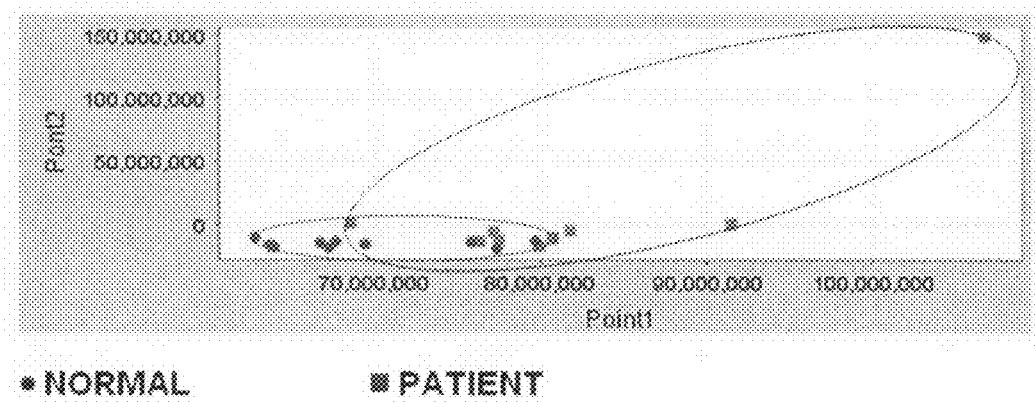
FIG. 4 shows results of a principal component analysis and a discriminant analysis, which are obtained by analyzing a fraction (fraction 3) acquired with an organic solvent extraction after hydrolyzing a water layer remained after obtaining the fraction 2.
Figure 4:
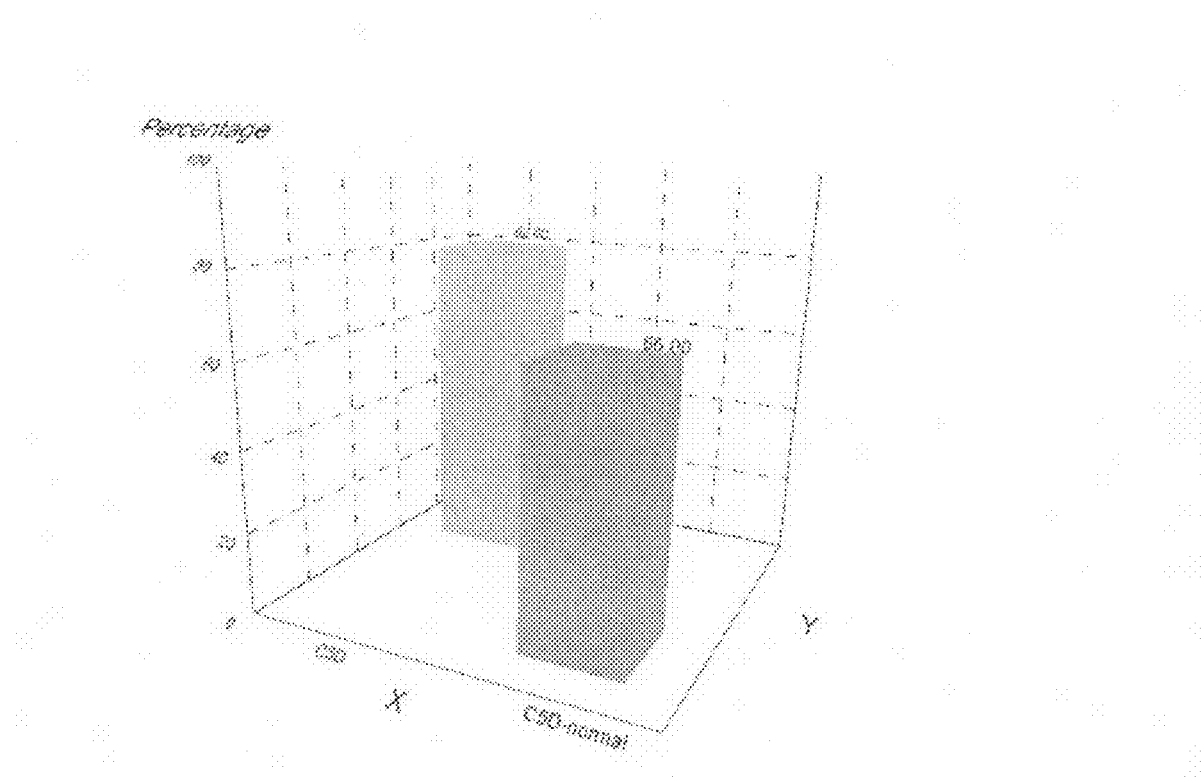
Figure 5:
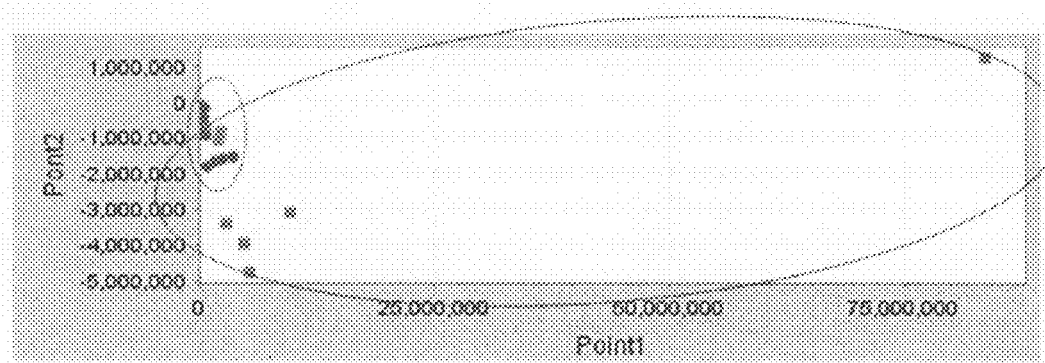
FIG. 5 shows results of a principal component analysis and a discriminant analysis, which are obtained by analyzing a fraction (fraction 4) acquired with an organic solvent extraction after adjusting the fraction 3 to be pH 13 using $K_2CO_3$.
Figure 5:
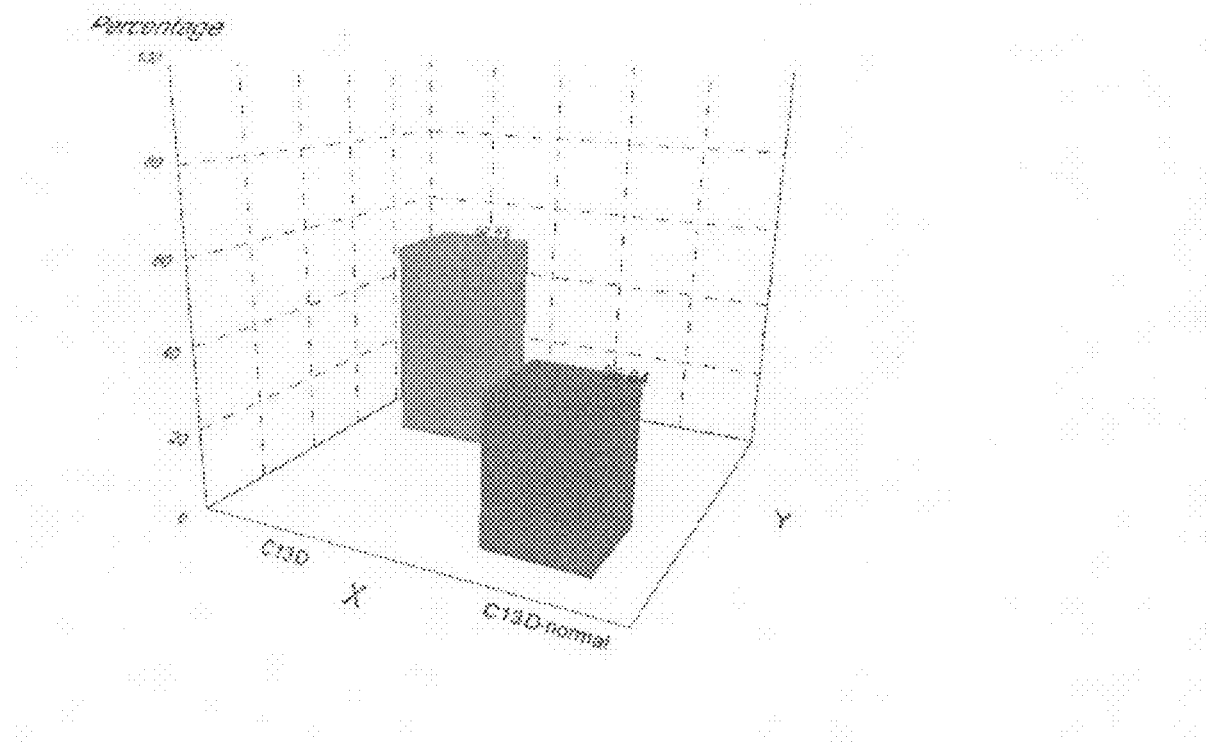

As a result, clustering patterns discriminating between the group of the normal people and the group of patients were exhibited in the principal component analysis of the fraction 2 (fraction obtained by the liquid-liquid extraction at pH 5.2 after the solid phase extraction, FIG. 3) and the fraction 3 (fraction obtained by the liquid-liquid extraction at pH 5.2 after the hydrolysis, FIG. 4). In particular, according to the result of discriminant analysis, when the statistical analysis was conducted with the fraction 2, the prostatic hypertrophy patient and the normal person were discriminated in the high accuracy (77% or more). Therefore, it was judged as follows: when the sample is extracted as a method for obtaining the fraction 2 (liquid-liquid extraction at pH 5.2 after the solid phase extraction), the metabolic change of the prostatic hypertrophy can be detected best, so that the metabolic difference between the prostatic hypertrophy patient and the normal person can be discriminated in the high accuracy. In the mean time, the difference of the clustering patterns was remarkably decreased in the principal component analysis of the fraction 1 (fraction analyzed immediately after the solid phase extraction, FIG. 2) and the fraction 4 (fraction analyzed after the liquid-liquid extraction at pH 13 after the hydrolysis, FIG. 5) and the diagnosis accuracy of the discriminant analysis was not good (i.e., 57% or less).

As described above, according to the invention, the whole metabolites included in the biological sample are effectively extracted and analyzed with a high-sensitive analysis device, so that the metabolite profile can be effectively measured. With the result, the statistical verification is conducted. Accordingly, when a disease appears or when administrating an extrinsic material, it is possible to measure the change of the metabolites in the organism, effectively and appropriately.

While the invention has been shown and described with reference to certain preferred embodiments thereof, it will be understood by those skilled in the art that various changes in form and details may be made thereto without departing from the spirit and scope of the invention as defined by the appended claims.

What is claimed is:

1. A method for detecting characteristic general difference of metabolites between biological sample groups, the method comprising the steps of:

extracting metabolites from a biological sample group and a control group without targeting a specific metabolite, by (i) extracting fraction 1 using a solid phase extraction method; (ii) separating fraction 2 from the fraction 1 using a liquid-liquid extraction method after making the fraction 1 buffered at pH 5~5.5; (iii) separating fraction 3 from leftover liquid phase left after separating the fraction 2, which is performed using a liquid-liquid extraction method after making the leftover liquid phase hydrolyzed by enzymes; and (iv) separating fraction 4 from leftover liquid phase left after separating the fraction 3, which is performed using a liquid-liquid extraction method after making the leftover liquid phase buffered at pH 13~13.5;

performing chromatography on each fraction with a chromatography analysis device;

converting a result of the chromatography into numerical values capable of being statistically processed;

analyzing the numerical values from the biological sample group and the numerical values from the control group with principal component analysis and discriminant analysis to detect comprehensive difference between the numerical values from the biological sample group and the numerical values from the control group; and determining whether there is characteristic difference between the metabolites from the biological sample group and the metabolites from the control group.

2. The method according to claim 1, wherein β-glucuronidase and arylsulfatase are used in the hydrolysis.

3. The method according to claim 1 wherein the chromatography analysis device has a mass spectrometry mounted to a gas chromatography.

4. The method according to claim 1, wherein the step of converting is performed by dividing a total analysis time by a unit time interval and determining the areas or heights of chromatogram peaks that are of the highest value exhibited during the unit time interval as a representative value during the unit time interval.

* * * * *